United States Patent [19]

Tenniswood

[11] Patent Number: 5,738,519

[45] Date of Patent: Apr. 14, 1998

[54] DENTAL SUCTION DEVICE

[76] Inventor: James R. Tenniswood, 1008 8th Ave., Okeechobee, Fla. 34972

[21] Appl. No.: 407,223

[22] Filed: Mar. 21, 1995

[51] Int. Cl.$^6$ ............................................. A61C 17/06
[52] U.S. Cl. ............................................................ 433/92
[58] Field of Search ................................. 433/92; 604/319

[56] References Cited

U.S. PATENT DOCUMENTS

| | | | |
|---|---|---|---|
| 855,888 | 6/1907 | Hecker | 433/91 |
| 2,759,476 | 8/1956 | Henderson | 604/319 |
| 2,864,166 | 12/1958 | Shaw | 433/92 |
| 3,017,866 | 1/1962 | Thompson | 433/92 |
| 3,078,579 | 2/1963 | Jones et al. | |
| 3,138,873 | 6/1964 | Bishop | 433/92 |
| 3,305,927 | 2/1967 | Mitchell | 433/92 |
| 3,457,645 | 7/1969 | Swanson | 433/92 |
| 3,520,300 | 7/1970 | Flower, Jr. | |
| 3,612,089 | 10/1971 | Beguiristain | 433/91 |
| 4,245,989 | 1/1981 | Folkenroth et al. | 433/92 |
| 5,017,135 | 5/1991 | Meyer | 433/92 |
| 5,127,411 | 7/1992 | Schoolman et al. | 128/863 |
| 5,282,744 | 2/1994 | Meyer | 433/92 |

FOREIGN PATENT DOCUMENTS

| 1220255 | 1/1971 | United Kingdom | 433/92 |
|---|---|---|---|

OTHER PUBLICATIONS

PAC*FAB Brochure; Triton high rate sand filters, 2 pages.

*Primary Examiner*—Cary E. O'Connor
*Attorney, Agent, or Firm*—Edward J. Timmer

[57] ABSTRACT

Dental suction device comprising a collection tank, a motor operably associated with the collection tank for generating a relative vacuum therein, and a flapper release valve disposed inside a downwardly extending drain conduit communicated to the collection tank and opening when the motor is inoperative for draining the contents of the collection tank through the drain conduit when the motor is inoperative. The collection tank comprises a reinforced plastic tank having an enlarged internal capacity to provide at least day-long collection such that there is no interruption in the operation of the dental suction device during a working day.

7 Claims, 2 Drawing Sheets

DENTAL SUCTION DEVICE

FIELD OF THE INVENTION

The present invention relates to dental suction or evacuator devices for evacuating saliva, water, tooth chips, and other fluid entrained debris from the mouth of a dental patient.

BACKGROUND OF THE INVENTION

Modern dental care facilties include one or more work stations or operatories where dental procedures are performed on the patient and where a suction or evacuator device is provided to remove water, tooth chips, and other fluid entrained debris from the patient's mouth during the procedure. For example, during drilling and filling of tooth cavities, tooth chips and debris are generated in the patient's mouth. Water typcially is sprayed on the tooth being repaired to facilitate the procedure. The water and tooth chips and debris entrained in the water are removed during the procedure by an aspirator tip placed in the mouth and connected to a central suction or evacutor device that may service all of the operatories. The suction device typically comprises a suction fan or blower associated with a central collection tank of limited capacity (e.g. 5 gallons or less) into which the water, tooth chips, and other debris are drawn and collected.

Many commercially available suction devices provide a limit switch in the collection tank to prevent overfilling of the tank during the conduct of dental procedures during the normal work day. When the collection tank is filled to the limit switch level, the switch is actuated to terminate energization of the vacuum fan or blower. When the relative vacuum in the collection tank is terminated, a drain valve is operable to drain the tank contents to a suitable drain pipe, such as plumbing or septic drain of the facility. A tank drain valve actuated by differential pressure between the inside and outside of the collection have been employed to this end.

A disadvantage of such dental suction devices has been associated with the termination of the relative vacuum in the collection tank during the work day so as to permit draining of the collection tank. This loss of vacuum at the collection tank results in a loss of the function of the aspirator tip(s) at the operatories and thus interrupts the particular dental procedures being carried out. The loss of function of the aspirator tip(s) can cause patient concern or anxiety and results in lost working time during the day as well as frustration for the dentist due to interruptions during treatment.

In addition, the dental suction devices in use today employ stainless steel and other costly materials for a collection tank to resist corrosive effects of the water and debris collected from patients' mouths during the day. Moreover, the vacuum suction fan or blower, tank overfill switch, tank drain valve, and other tank components increase the cost of the suction device such that a typcial cost to the dental practioner of a wet/dry suction device can be on the order of $5000–$7500.

An object of the present invention is to provide an improved dental suction device that overcomes these disadvantages of conventional commercially marketed dental wet/dry suction devices.

SUMMARY OF THE INVENTION

The present invention provides an improved wet/dry dental suction device comprising a collection tank adapted to be communicated to one or more aspirator tips, a vacuum-generating electric motor operably associated with the collection tank for generating a relative vacuum therein, and a release valve communicated to the collection tank for draining the contents of the collection tank when the vacuum motor is inoperative. The collection tank comprises a plastic fiberglass reinforced tank having an enlarged internal capacity to provide at least day-long collection such that there is no interruption in the operation of the dental suction device during a working day. Preferably, the collection tank has an internal capacity or volume of at least about 35 gallons to this end.

In one embodiment of the invention, the collection tank comprises a one-piece fiberglass reinforced plastic tank. The release valve comprises a plastic housing having a pipe section of given diameter connected to the collection tank, a valve housing section connected to the pipe section and having a diameter greater than the given diameter, and a flapper valve separating the pipe section and the valve housing and operable under the weight of the tank contents to drain the collection tank contents when the relative vacuum in the collection tank is terminated and ambient pressure is present therein.

The above and other objects of the invention will become mnore readily apparent from the following detailed description and the following drawings.

DETAILED DESCRIPTION OF THE INVENTION

The present invention provides a reduced cost, improved wet/dry dental suction device for servicing one or more work stations or operatories where dental procedures are performed on patient(s) and where a suction or evacuator device is needed to remove water, tooth chips, and other fluid entrained debris from the patients' mouths during various procedures that may be performed.

Figure 1:
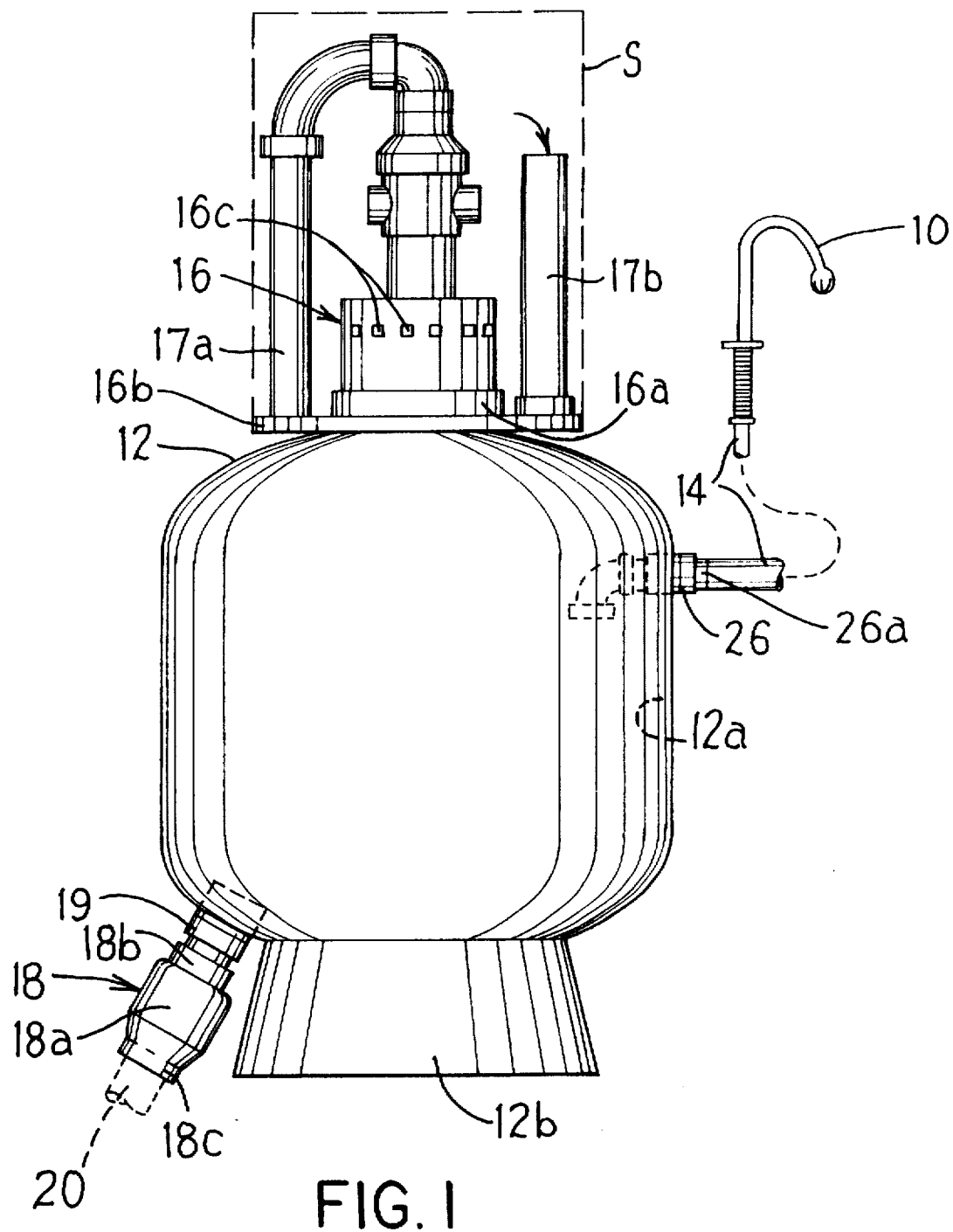
FIG. 1 is an elevational view of a dental suction device pursuant to an embodiment of the present invention with an aspirator tip shown in communication with a collection tank.
Figure 2:
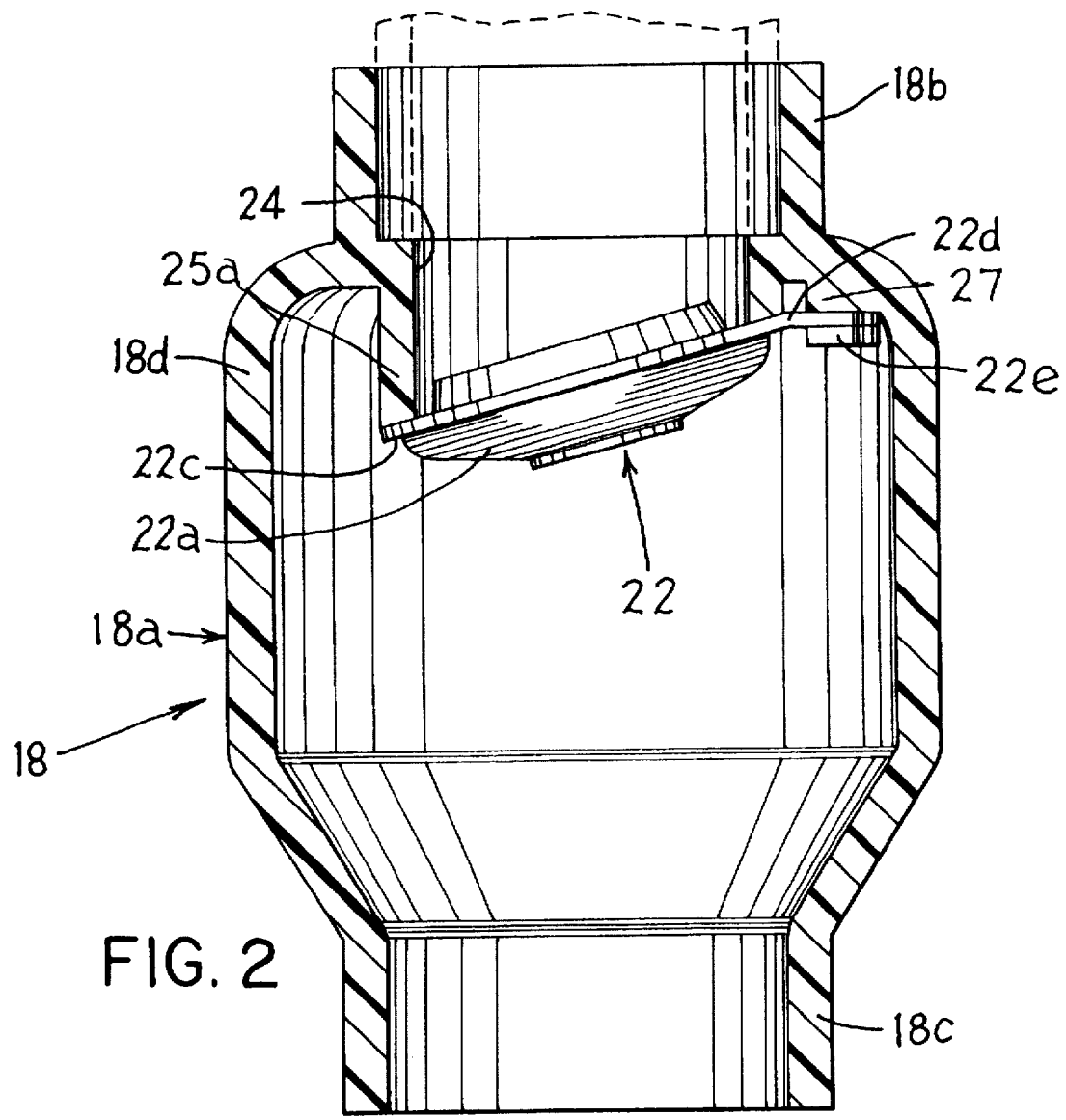
FIG. 2 is a sectional view of the automatic tank release valve.
Figure 3:
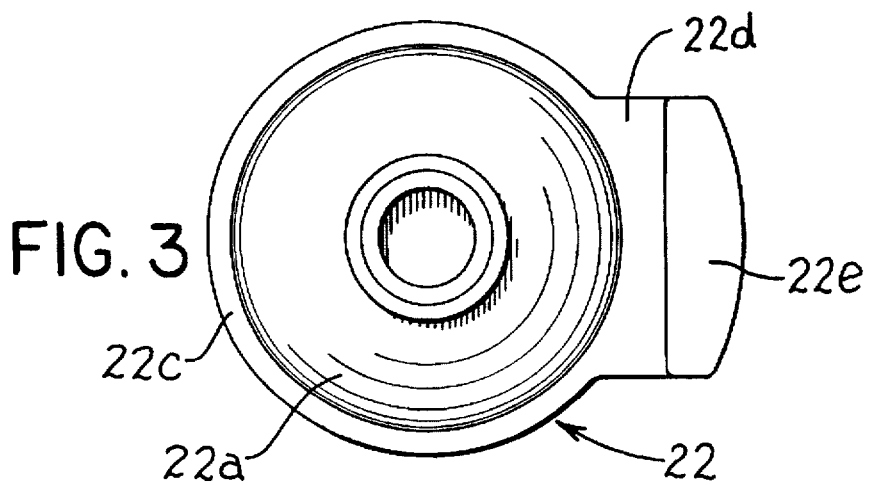
FIG. 3 is a bottom plan view of the flapper release valve.

Referring to FIGS. 1–3, a dental suction device in accordance with an embodiment of the invention is shown for purposes of illustration. The dental suction device is adapted for use with one or more conventional aspirator tips 10 (one shown) for positioning in a patient's mouth at respective operatories. The aspirator tips 10 form no part of the invention, however. Each aspirator tip 10 is communicated to the internal chamber 12a of a collection tank 12 by a respective conventional flexible conduit 14 (one shown).

A vacuum-generating electric motor/blower 16 is mounted on the top of the collection tank 12 by a PVC (polyvinylchloride) support bracket 16a and support plate 16b. The motor/blower 16 communicates via an aperture in the tank wall with the tank interior chamber 12a for evacuating the chamber 12a. A cylindrical shroud or cover S (shown in dashed lines for convenience) is disposed on the support plate 16b to enclose the motor/blower 16. Alternately, the vacuum-generating electric motor 16 can be disposed at a location remote from the colection tank 12 and communicated thereto by suitable conduits (not shown) to this same end. The vacuum-generating motor 16 is effective to generate a relative vacuum in the collection tank chamber 12a and thus at the aspirator tip(s) 10. To this end, the vacuum motor 16 can comprise a three-stage AC industrial/commercial electrical motor/blower available as Ametek model 114787 from Lamb Electric Division, Kent, Ohio.

The motor/blower 16 includes a tubular air inlet conduit 17a having an opening at the support plate 16b through which opening air is sucked in by the motor/blower. Air is discharged or exhausted from the motor/blower 16 via motor/blower housing slots or openings 16c and exhausted to the chamber within the shroud S and support plate 16b for discharge as indicated by the arrow in FIG. 1 through air outlet conduit 17b having an opening at the top and at the support plate 16b where the exhaust air is discharged to ambient. The outlet conduit 17b is optional since an opening through the support plate 16b to ambient can also serve to exhaust air from the chamber defined between the shroud S and support plate 16b.

When the vacuum motor 16 is inoperative (i.e. shut-off), ambient pressure is provided in the tank chamber 12a by reversed airflow through the inoperative vacuum motor/blower. The collection tank 12 can be disposed at myriad locations in the dental facility, such as, for example, conveniently in the basement, utility room, or other appropriate location inside or outside the facility.

A release valve 18 is communicated to the collection tank 12 for draining its contents when the vacuum motor 16 is rendered inoperative (i.e. shut off). The release valve 18 comprises a plastic (e.g. PVC) central housing 18a having a first pipe section 18b of given diameter (e.g. 2 inch inner diameter) at one end connected to the collection tank 12 by a conventional PVC compression fitting 19 (2 inch) or other means disposed on the tank wall and a second pipe section 18c of similar diameter at the opposite end communicated to a drain pipe 20, such as sewer pipe, septic system pipe and the like. The valve housing 18a has an enlarged cross-section. For example, the valve housing 18a includes a 4 inch diameter cylindrical section 18d connected to the first pipe connector section 18b and receiving a flapper valve 22 therein. The cylindrical section 18d is connected to a conical tapering section that, in turn, is connected to the second pipe connector section 18c as shown best in FIG. 2.

The flapper valve 22 separates the first pipe section 18b and the enlarged cylindrical section 18d of the valve housing 18a. The flapper valve 22 is operable under the weight of the contents of the collection tank 12 to drain the contents to the drain pipe 20 when the relative vacuum in the collection tank is terminated and ambient pressure is present therein.

The flapper valve 22 includes a rigid central valve section 22a made of PVC for closing the opening 24 between the first pipe section 18b and the cylindrical section 18d of the valve housing 18a. The flapper valve 22 includes a peripheral, annular flexible (e.g. reinforced rubber) sealing rim 22c in which the central PVC valve section 22a is held by a PVC weld. The rim 22c seals on the annular shoulder 25a of the extension of valve housing extension 18a. The flapper valve rim 22c includes an integral radial reinforced rubber hinge 22d extending from the rim 22c to a rigid (e.g. PVC) attachment tab 22e. The tab 22e is fastened to a shoulder 27 of the valve housing by a PVC weld or other attachment means such that the flapper valve 22 can flex at hinge 22d during operation to release the contents of the collection tank 12 to the drain pipe 20 when the relative vacuum in the collection tank is terminated and ambient pressure is present therein. That is, the weight of the tank contents opens the flapper valve 22 to drain when the relative vacuum in the tank is terminated and ambient pressure is present therein.

A release valve of the type described is commercially available as Series 1520-20 PVC swing check valve (2 inch) from Flo Control, Inc., subsidiary of Buffton Corp. 3210 Winona, Ave., Burbank, Calif.

The collection tank 12 comprises a low cost fiberglass reinforced plastic tank molded as a one-piece tank with an integral or attached stand or base 12b at the bottom. The tank includes a conventional PVC compression fitting 26 (2 inch fitting) fastened on the tank wall and communicating with the interior chamber 12a of the collection tank 12. The conduit 14 is connected to the compression fitting 26 so as to communicate the aspirator 10 to the tank chamber 12a.

The collection tank 12 is provided with the enlarged internal chamber 12a having a internal volume or capacity to provide at least day-long collection (e.g. day-long collection is for 12 hours or more) of fluids from one or more aspirator tips 10 in use such that there is no interruption in the operation of the dental suction device during each working day. This is advantageous to prevent loss of function of the aspirator tips 10 and thus to avoid interruption of dental procedures being carried out at the operatories, thereby providing more working time in the day. Moreover, this is advantageous from a patient perspective to prevent loss of function of the aspirator tip in the patient's mouth and resulting patient concern or anxiety.

The volume or capacity of the tank chamber 12a for servicing up to 8 operatories (each having a single aspirator tip 10) to provide interruption-free, day-long (12 hours) collection is at least about 35 gallons. This internal volume of the tank chamber 12a is more than adequate for servicing up to 8 operatories to provide interruption-free, day-long operation. A collection tank 12 having a 60 gallon tank internal volume is advantageous to provide 35 gallons of usable internal volume or capacity for collection of liquid and to maintain the upper level of collected liquid in the tank at a distance from the motor/blower 16 to avoid harmful suction of liquid in the tank into the motor/blower 16. For servicing additional operatories, one or more additional dental suction devices of the invention can be used depending upon the number of additional operatories to be serviced.

In accordance with the invention, the relative vacuum in the collection tank 12 is not interrupted by a overfill switch of the type and in the manner used in the prior suction devices during a working day in order to effect periodic drainage of the tank contents. The present invention does not need to employ an overfill switch to this end. In typical operation, the collection tank 12 is drained at the end of each day of operation when the electrical power to the suction device (i.e. motor/blower 16) is discontinued during non-working hours. The release valve 18 then is automatically opened by the weight of the tank contents to drain the contents to the drain pipe 20. That is, the flapper valve 22 is opened under the weight of the tank contents to this end.

The dental suction device of the present invention is advantageous as a result of its reduced cost (e.g. $500 to $700) as compared to the cost of prior dental suction systems which cost an order of magnitude more. Moreover, the dental suction device allows the conduct of dental procedures all day long without interruption to drain the collection tank, and yet provides automatic drainage of the collection tank at optimum times outside normal working hours (i.e. at non-working hours when electrical power to the dental suction device is terminated).

Although the invention has been described in terms of specific embodiments thereof, it is understood that modifications and changes can be made thereto within the scope of the invention and appended claims.

I claim:

1. A dental suction device comprising a floatless collection tank having a lower annular tank wall, a tank inlet conduit communicated to an aspirator and terminating in said collection tank in an inverted conduit elbow that deflects entering fluid and solid debris from said aspirator downwardly toward said lower tank wall for collection proximate a bottom of said collection tank, a motor operably associated with said collection tank for generating a relative vacuum therein, and a flapper release valve disposed inside a downwardly extending drain conduit disposed on and communicated to said collection tank and opening in a downward direction for draining the fluid and solid debris collected in said collection tank through said drain conduit when said motor is inoperative, said collection tank comprising a reinforced plastic tank having an enlarged internal capacity of at least about 35 gallons to provide at least day-long collection such that there is no interruption in the operation of said motor during a working day, whereby said suction device can collect said entering fluid and solid debris without the need for interruption of said motor during a working day.

2. The device of claim 1 wherein said collection tank comprises a one-piece fiberglass reinforced plastic tank.

3. The device of claim 1 wherein said release valve comprises a plastic housing having a pipe section of given diameter connected to said collection tank, a valve housing section connected to said pipe section and, having a diameter greater than said given diameter, and a flapper valve separating said pipe section and said valve housing and operable under the weight of the tanks contents to drain the collection tank contents when the relative vacuum in said collection tank is terminated.

4. The device of claim 3 wherein said flapper valve includes an integral hinge that is attached to said valve housing section.

5. The device of claim 1 wherein said vacuum motor comprises a three-stage vacuum motor.

6. The device of claim 5 wherein said vacuum motor is disposed on said collection tank.

7. A dental suction device comprising a floatless collection tank having a lower annular tank wall, a tank inlet conduit communicated to an aspirator and terminating in said collection tank in an inverted conduit elbow that deflects entering fluid and solid debris from said aspirator downwardly toward said lower tank wall for collection proximate a bottom of said collection tank, a motor operably associated with said collection tank for generating a relative vacuum therein, and a flapper release valve disposed inside a downwardly extending drain conduit disposed on and communicated to said collection tank and opening in a downward direction for draining the fluid and solid debris collected in said collection tank through said drain conduit, said drain conduit communicating with said collection tank above the bottom thereof, said collection tank comprising a reinforced plastic tank having an enlarged internal capacity of at least about 35 gallons to provide at least day-long collection such that there is no interrruption in the operation of said motor during a working day, whereby said suction device can collect said entering fluid and solid debris without the need for interruption of said motor during a working day.

* * * * *